United States Patent [19]
Sarges et al.

[11] 3,991,207
[45] Nov. 9, 1976

[54] COMBINATION THERAPY FOR PARKINSON'S DISEASE

[75] Inventors: Reinhard Sarges, Mystic; Albert Weissman, Niantic, both of Conn.

[73] Assignee: Pfizer Inc., New York, N.Y.

[22] Filed: Mar. 18, 1971

[21] Appl. No.: 125,804

[52] U.S. Cl. ............................. 424/319; 260/574; 260/575; 424/330
[51] Int. Cl.² ..................................... A61K 31/20
[58] Field of Search ............ 424/319, 330; 260/574, 260/575

[56] References Cited
UNITED STATES PATENTS

| | | | |
|---|---|---|---|
| 3,462,534 | 8/1969 | Greenlard et al. ................. | 424/308 |
| 3,557,292 | 1/1971 | Bartholini .......................... | 424/319 |
| 3,579,582 | 5/1971 | Symon ............................... | 260/574 |

OTHER PUBLICATIONS

J. Med. Chem. 9, 830–832 (1966).
Merck Index 8th ed. p. 699 (1968).

*Primary Examiner*—Leonard Schenkman
*Attorney, Agent, or Firm*—Connolly and Hutz

[57] ABSTRACT

Substituted 1,2,3,4-tetrahydro-1-naphthylamines, or their acid addition salts, as potentiating agents in combination therapy with L-Dopa for control of the symptoms of Parkinson's disease. N,N-Dimethyl-5-methoxy-8-chloro-1,2,3,4-tetrahydro-1-naphthylamine is the preferred embodiment.

3 Claims, No Drawings

COMBINATION THERAPY FOR PARKINSON'S DISEASE

BACKGROUND OF THE INVENTION

This invention relates to the use of certain 1-aminobenzocycloalkane compounds. More particularly it is concerned with various substituted 1,2,3,4-tetrahydro-1-naphthylamines, and their acid addition salts, which are useful as potentiating agents in combination therapy with the L-isomer of 3,4-dihydroxyphenylalanine (L-Dopa) in the treatment of Parkinson's Disease.

Parkinson's disease is a chronic neurological disorder characterized by tremor, rigidity of the limbs and poverty of movement (hypokinesia). In most patients, initial symptoms develop in the fifth or sixth decade of life and gradually progress, death usually occurring about 10 years after onset. Parkinson's disease is common, its estimated prevalence being 1 in 1,000 of the population.

Known causes of Parkinson's disease include viral infection (encephalitis lethargica), toxins (manganese, carbon monoxide), vascular disease (atherosclerosis) and drugs (phenothiazines, haloperidol, reserpine). In most cases, however, no cause can be identified. Pathological examination of the brain reveals widespread degenerative changes in the basal ganglia, particularly the substantia nigra and corpus striatum.

During the past decade a new approach to Parkinson's disease has evolved, culminating in the introduction of L-Dopa, a drug which is likely to have an important impact on future management of this syndrome (Calne, D. B. and M. Sandler, Nature 226, Apr. 4, 1970).

No drug is ideal, and L-dopa is no exception. A significant proportion of patients have to discontinue their treatment owing to unpleasant side effects, the most common being severe nausea and vomiting. A more serious side effect is postural hypotension, the inability to maintain a normal blood pressure while standing, which can result in fainting and giddiness and is dangerous under certain circumstances.

SUMMARY OF THE INVENTION

In accordance with the present invention, it has now been surprisingly found that various substituted 1-aminocycloalkanes are extremely useful as potentiating agents of the central nervous system effects of L-Dopa. The compounds of this invention active as potentiating agents are all selected from the group consisting of 1-aminocycloalkane bases of the formula:

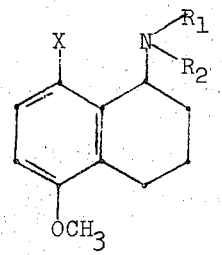

and the pharmaceutically acceptable acid addition salts thereof, wherein X is hydrogen, chlorine, bromine, or methoxy; $R_1$ and $R_2$ are each hydrogen or lower alkyl having from one to three carbon atoms. The preferred embodiment is N,N-dimethyl-5-methoxy-8-chloro-1,2,3,4-tetrahydro-1-naphthylamine. Although the tests and dosage levels reported herein and in the claims are based on use of the racemic mixtures of these potentiating agents, as normally obtained in chemical synthesis, it is believed that the potentiating activity may reside in the S-isomer component of these mixtures. This is a subject of continuing investigation. Those optical isomers with the S-configuration have previously found use as antidepressant agents. Recently other antidepressants, namely the tricyclic antidepressants, have been used in combination with L-Dopa with no adverse side effects, but with no special advantage.

In the present invention, a ratio of L-Dopa to substituted 1,2,3,4-tetrahydro-1-naphthylamine of from about 40 to 1 to about 1 to 1 is effective. An effective daily dose for treating the symptoms of Parkinson's disease comprises from about 7 to about 80 mg/kg body weight of L-Dopa and from about 2 to about 7 mg/kg body weight of the substituted 1,2,3,4-tetrahydro-1-naphthylamine.

DETAILED DESCRIPTION OF THE INVENTION

In accordance with the processes employed for preparing the L-Dopa potentiating compounds of this invention, various alternate methods are provided depending upon the actual starting materials and/or intermediates utilized in this connection. For instance, a known 5-alkoxy-3,4-dihydro-1(2H)-naphthalenone, like 5-methoxy-8-chloro-3,4-dihydro-1(2H)-naphthalenone [H. W. Huffman, Journal of Organic Chemistry, Vol. 24, p. 1759 (1959)] can be reacted in the presence of titanium tetrachloride with an appropriate secondary amine of the formula $R_1R_2NH$, wherein $R_1$ and $R_2$ are each as previously defined, to give an intermediate enamine, which is then reduced either with formic acid, or with lithium borohydride in the presence of formic acid, to yield the desired final product, e.g., dl-N,N-dimethyl-5-methoxy-8-chloro-1,2,3,4-tetrahydro-1-naphthylamine. Conversely, when the initial condensation reaction is carried out with a primary amine of the formula $R_1NH_2$ and the resultant Schiff base is reduced with sodium borohydride, there is obtained a 5-alkoxy-1,2,3,4-tetrahydro-1-naphthylamine like dl-N-methyl-5-methoxy-8-chloro-1,2,3,4-tetrahydro-1-naphthylamine, i.e., a secondary amine compound.

In like manner, when a known compound such as 5-methoxy-3,4-dihydro-1-(2H)-naphthalenone [see Chemical Abstracts, Vol. 40, p. 8973 (1946)] is subjected to these same series of reactions, the corresponding final product obtained lacks a substituent group at the 8-position of the molecule and can be further reacted with an appropriate alkanoyl halide of choice in the presence of aluminum chloride to give the corresponding 8-alkanoyl derivative thereof, i.e., a 5-alkoxy-8-alkanoyl-1,2,3,4-tetrahydro-1-naphthylamine compound like dl-N,N-dimethyl-5-methoxy-8-formoyl-1,2,3,4-tetrahydro-1-naphthylamine.

On the other hand, a 5-alkoxy-3,4-dihydro-1(2H)-naphthalenone compound, such as 5-methoxy-3,4-dihydro-1(2H)-naphthalenone, can be simply converted to its oxime via hydroxylamine and the latter intermediate reduced with hydrogen in the presence of a palladium-on-carbon catalyst to give the resultant primary amine, i.e., the corresponding 5-alkoxy-1,2,3,4-tetrahydro-1-naphthylamine compound. Bromination of the latter intermediate using ferric chloride as catalyst then affords the corresponding 8-bromo derivative, which, in turn, yields dl-N,N-dimethyl-5-alkoxy-8-bromo-1,2,3,4-tetrahydro-1-naphthylamine on treatment with excess formaldehyde in a formic acid medium.

The starting materials employed for preparing the potentiating compounds of this invention are, for the most part, known compounds like 5-methoxy-3,4-dihydro-1(2H)-naphthalenone and its 8-chloro derivative, or else they are easily prepared by those skilled in the art from more readily available materials using conventional organic procedure.

Resolution of the racemic primary and/or secondary 1-aminobenzocycloalkane compounds of this invention is then accomplished in a conventional manner, using N-acetyl-L-tyrosine as the initial resolving agent therefor in a lower alcoholic solvent medium (e.g., methanol), whereby the less soluble diastereoisomeric salt is subsequently formed and isolated. Treatment of the alcoholic mother liquors obtained from above with D(-)mandelic acid then gives the corresponding diastereoisomeric salt of the other optical isomer. In this way, a compound such as dl-5-methoxy-8-chloro-1,2,3,4-tetrahydro-1-naphthylamine is ultimately separated into its respective R- and S-optical antipodes.

The acids which are used to prepare the pharmaceutically-acceptable acid addition salts of this invention are those which form non-toxic acid addition salts containing pharmacologically acceptable anions, such as the hydrochloride and sulfate, when reacted with the aforementioned 1-aminobenzocycloalkane base compounds. Preferred acids for use in this connection include hydrochloric acid, hydrobromic acid, hydroiodic acid, nitric acid, sulfuric acid, phosphoric acid, acetic acid, lactic acid, citric acid, tartaric acid, oxalic acid, gluconic acid, saccharic acid, benzoic acid, succinic acid, maleic acid, methanesulfonic acid, ethanesulfonic acid, benzenesulfonic acid, p-toluenesulfonic acid, picric acid, amsonic acid (4,4'-diaminoatilbene-2,2'-disulfonic acid) and pamoic acid (1,1'-methylene-bis-2-hydroxy-3-naphthoic acid).

As previously indicated, the 1-aminobenzocycloalkane compounds of this invention are valuable as psychotherapeutic agents, and the S-configuration isomers of these compounds, when used in combination therapy with L-Dopa, have the ability to potentiate the action of the latter drug in regard to central nervous system activity. Two widely-accepted tests for the evaluation of agents designed for the treatment of Parkinson's disease are the well known trifluoperazine and haloperidol challenges. In accordance with either of these procedures, the test animal is rendered cataleptic by the administration of trifluoperazine or haloperidol, and the agent under evaluation is administered to determine its ability to reverse the syndrome. The validity of these tests is supported by the fact that L-Dopa, which has found wide acceptance in the treatment of Parkinson's disease in humans, gives a reversal of the above mentioned challenges. Animal tests have shown that the potentiating agents of the present invention in combination with L-Dopa provide equivalent results at lower L-Dopa administration levels and provide more marked effects at equivalent L-Dopa administration levels. Accordingly, it is reasonable to predict that these agents will exhibit a similar potentiating effect when administered in combination with L-Dopa in the treatment of Parkinson's disease in humans. For instance, dl-N,N-dimethyl-5-methoxy-8-chloro-1,2,3,4-tetrahydro-1-naphthylamine, a typical and preferred agent of the present invention, when co-administered with L-Dopa, has been found to cause significant skeletal muscle relaxation in rats when administered by the intraperitoneal route, following a trifluoperazine or haloperidol challenge. The catalepsy normally seen after administration of either of these agents is absent.

The herein described compounds can be administered to humans by either the oral or parenteral routes of administration. In general, they will ordinarily be administered in dosages ranging from about 2 mg. to about 7 mg. per kg. of body weight per day, although variations will necessarily occur depending upon the weight and condition of the subject being treated and the particular route of administration chosen. L-Dopa will be administered in conjunction with the above dosage in the amount of about 7 to about 80 mg. per kg. of body weight per day, the precise amount also being dependent upon the weight and condition of the subject.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

For purposes of parenteral administration, solutions of these particular 1-aminobenzocycloalkanes in sesame or peanut oil or in aqueous propylene glycol or N,N-dimethylformamide may be employed, as well as sterile aqueous solutions of the corresponding water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

PREPARATION A

A solution consisting of 31.5 g. (0.15 mole) of 5-methoxy-8-chloro-3,4-dihydro-1(2H)-naphthalenone [H. W. Huffman, *Journal of Organic Chemistry*, Vol. 24, p. 1759 (1959)] dissolved in 600 ml. of ethanol was treated with 30 ml. of phenylhydrazine in the presence of 120 ml. of glacial acetic acid and the mixture thereafter heated on a steam bath for 30 minutes. Upon cooling, the resulting phenylhydrazone crystallized from solution and was subsequently collected by means of suction filtration to afford a nearly quantitative yield (45 g.) of the aforesaid derivative, m.p. 182°–183° C.

Anal. Calc'd for $C_{17}H_{17}ClN_2O$: C, 67.87; H, 5.69; N, 9.32. Found: C, 67.81; H, 5.79; N, 9.27.

The above phenylhydrazone (45 g., 0.15 mole) was then suspended in 2000 ml. of glacial acetic acid and the resulting suspension was thereafter treated with 111 g. of activated zinc dust, added in small portions during the course of a ten-minute period. The resulting reaction mixture was then stirred and heated to 70° C., and held at that point for 3 hours, followed by stirring at room temperature (~25° C.) for 20 hours. After filtering the spent mixture to remove excess zinc particles, the filtrate thus obtained was subsequently concentrated in vacuo to afford a residue that was then diluted with 500 ml. of water. The resulting aqueous solution was then adjusted to pH 4.5 with 6N hydrochloric acid and extracted with three-200 ml. portions of diethyl ether to remove the aniline by-product. Upon rendering the aqueous layer strongly basic with 4N sodium hydroxide solution, followed by extraction of the latter with three-300 ml. portions of diethyl ether, there were obtained ethereal extracts containing the desired free organic base compound. The latter were then combined, washed with water and dried over anhydrous magnesium sulfate to give a dried filtrate that was subsequently concentrated under reduced pressure to afford a residual oil.

This oil, which consisted essentially of pure dl-5-methoxy-8-chloro-1,2,3,4-tetrahydro-1-naphthylamine, was then dissolved in diethyl ether and treated with dry hydrogen chloride gas to give the corresponding hydrochloride salt, m.p. 269°–272° C. The yield of pure dl-5-methoxy-8-chloro-1,2,3,4-tetrahydro-1-naphthylamine hydrochloride amounted to 31.4 g. (82%), m.p. 272°–273° C.

Anal. Calc'd for $C_{11}H_{14}ClNO.HCl$: C, 53.24; H, 6.10; N, 5.65. Found: C, 53.28; H, 6.13; N, 5.54.

PREPARATION B

In a dry three-necked, round-bottomed reaction flask equipped with magnetic stirrer, internal thermometer and dropping funnel, there were placed a pre-cooled solution (0.5° C.) of 15.8 g. (0.075 mole) of 5-methoxy-8-chloro-3,4-dihydro-1(2H)-naphthalenone and 29.78 ml. (0.45 mole) of anhydrous dimethylamine in 225 ml. of benzene in accordance with the general procedure described by W. A. Wise et al. in the *Journal of Organic Chemistry*, Vol. 32, p. 213 (1967) for the preparation of enamines. Stirring was then commenced, while 4.13 ml. (0.038 mole) of titanium tetrachloride in 25 ml. of benzene was slowly added to the aforesaid solution in a dropwise manner, while under a dry nitrogen atmosphere. During the addition, the temperature of the reaction mixture was kept below 10° C., while thereafterwards it was allowed to warm up slowly so as to attain room temperature (~25° C.). The resulting mixture was then stirred continuously at the latter point for a period of about 1–5 hours, i.e., until various aliquots showed almost complete conversion of the ketone to the enamine, as revealed by gas-liquid chromatographic analysis. At this point, the spent reaction mixture was filtered and the resulting solids twice slurried with 100 ml. portions of fresh benzene and filtered once again. The combined benzene filtrates were then evaporated under reduced pressure to give 18 g. of oily enamine, i.e., an almost quantitative yield of N,N-dimethyl-5-methoxy-8-chloro-3,4-dihydro-1-naphthylamine.

To the above enamine, there were then added 14 ml. of 98% formic acid introduced in a dropwise manner and this, in turn, resulted in gas evolution and heat generation (in accordance with the general procedure described by M. J. Leonard et al. in the *Journal of the American Chemical Society*, Vol. 79, p. 6210 (1957) for the reduction of enamines). The resulting reaction mixture was then stirred for 20 hours at room temperature (~25° C.) and thereafter diluted with 100 ml. of water. After adjusting the pH of the resulting aqueous solution to pH 1.0 with 6N hydrochloric acid, it was subsequently washed by means of extraction with diethyl ether. The washed aqueous layer was then readjusted to pH 12 with 4N sodium hydroxide solution and extracted three times with diethyl ether. The combined ether layers were then washed with water and dried over anhydrous magnesium sulfate. After removal of the drying agent by means of filtration, the dried ethereal filtrate was subsequently concentrated in vacuo to afford 14.5 g. (81%) of dl-N,N-dimethyl-5-methoxy-8-chloro-1,2,3,4-tetrahydro-1-naphthylamine as a residual oily amine.

The above oil product was then treated with dry hydrogen chloride gas in diethyl ether to give 16.2 g. (78%) of the corresponding hydrochloride salt, m.p. 186°–189° C. Recrystallization from methanol-acetone-diethyl ether then gave 11.96 g. (58%) of pure dl-N,N-dimethyl-5-methoxy-8-chloro-1,2,3,4-tetrahydro-1-naphthylamine hydrochloride, as the first crop of crystals, m.p. 191°–193° C.

Anal. Calc'd. for $C_{13}H_{18}ClNO.HCl$: C, 56.54; H, 6.94; N, 5.08 Found: C, 56.48; H, 6.98; N, 4.82.

Compounds of the following structure may also be prepared by the foregoing procedures:

| X | R₁ | R₂ |
|---|----|----|
| H | H | H |
| Br | CH₃ | CH₃ |
| OCH₃ | H | H |
| H | C₃H₇ | H |
| Cl | H | CH₃ |

EXAMPLE I

An apparatus consisting of four pedestals (rubber stoppers), larger circumference downward, centered on the angles of an isosceles trapezoid was employed. A catalepsy trial was conducted by placing a rat's two front paws onto the two stoppers describing the shorter base and the two hind paws onto the stoppers describing the longer base. If a rat remained in this awkward posture for 30 sec. he was judged to be cataleptic; if he moved his paws off the stoppers within 30 sec. he was judged to be non-cataleptic.

Rats were first treated with trifluoperazine or haloperidol at a high, cataleptic dose. Subsequently, they were treated with various combinations of N,N-dimethyl-5-methoxy-8-chloro-1,2,3,4-tetrahydro-1-naphthylamine and L-Dopa, as summarized in Tables 1 and 2, and then tested for counteraction of the cataleptic response.

Table 1 shows that the interaction of dl-N,N-dimethyl-5-methoxy-8-chloro-1,2,3,4-tetrahydro-1-naphthylamine, at the inactive (in this study) dose of 5.6 mg/kg., and L-Dopa at the ineffective dose of 100 mg/kg were synergistic in counteracting trifluoperazine catalepsy. Even when dl-N,N-dimethyl-5-methoxy-8-chloro-1,2,3,4-tetrahydro-1-naphthylamine was given at 3.2 mg/kg it appeared to interact with L-Dopa to reverse catalepsy.

Table 1

Blockade by dl-N,N-Dimethyl-5-methoxy-8-chloro-1,2,3,4-tetrahydro-1-naphthylamine + L-Dopa of catalepsy induced by trifluoperazine.

| Treatment (doses) in mg/kg i.p.* | | | % of rats exhibiting catalepsy at below times (hr) after treatment II | | |
|---|---|---|---|---|---|
| I | II | N | .5 | 1 | 2 |
| Saline | Saline | 25 | 96 | 96 | 100 |
| Saline | L-Dopa-(100) | 10 | 100 | 100 | 100 |
| dl-N,N-dimethyl-5-methoxy-8-chloro-1,2,3,4-tetrahydro-1-naphthylamine (3.2) | L-Dopa-(100) | 10 | 60 | 60 | 80 |
| dl-N,N-dimethyl-5-methoxy-8-chloro-1,2,3,4-tetrahydro-1-naphthylamine (5.6) | L-Dopa-(100) | 10 | 30 | 20 | 70 |
| dl-N,N-dimethyl-5-methoxy-8-chloro-1,2,3,4-tetrahydro-1-naphthylamine (5.6) | Saline | 10 | 100 | 100 | 100 |

*Treatment I given 1.5 hrs. after trifluoperazine; treatment II given 2 hrs. after trifluoperazine. Dose of trifluoperazine was 32 mg/kg i.p.

In a slightly different protocol using the haloperidol challenge (Table 2) dl-N,N-dimethyl-5-methoxy-8-chloro-1,2,3,4-tetrahydro-1-naphthylamine at 5.6 mg/kg i.p., given simultaneously with L-Dopa at 178 or 316 mg/kg i.p. also produced a synergistic, anticataleptic action.

Table 2

Blockade by dl-N,N-dimethyl-5-methoxy-8-chloro-1,2,3,4-tetrahydro-1-naphthylamine + L-Dopa of catalepsy induced by haloperidol.

| Treatment (doses) in mg/kg i.p.* | | | % of rats exhibiting catalepsy at below times (hr) after treatment II | | |
|---|---|---|---|---|---|
| I | II | N | 1 | 2 | 3 |
| Saline | Saline | 15 | 87 | 100 | 100 |
| None | L-Dopa-(178) | 5 | 100 | 100 | 100 |
| None | L-Dopa-(316) | 5 | 60 | 100 | 100 |
| dl-N,N-dimethyl-5-methoxy-8-chloro-1,2,3,4-tetrahydro-1-naphthylamine (5.6) | None | 5 | 80 | 100 | 100 |
| dl-N,N-dimethyl-5-methoxy-8-chloro-1,2,3,4-tetrahydro-1-naphthylamine (5.6) | L-Dopa-(178) | 5 | 60 | 100 | 100 |
| dl-N,N-dimethyl-5-methoxy-8-chloro-1,2,3,4-tetrahydro-1-naphthylamine (5.6) | L-Dopa-(316) | 5 | 20 | 40 | 100 |

*Treatment I and II were each given in separate injections 2 hrs. after haloperidol, 10 mg/kg i.p.

EXAMPLE II

Formulation of tablets and capsules of the pharmaceutical composition of this invention may be effected using the following ingredients:

| Capsules | mg/capsules |
|---|---|
| L-Dopa | 46.7 |
| N,N-Dimethyl-5-methoxy-8-chloro-1,2,3,4-tetrahydro-1-naphthylamine | 46.7 |
| Microcrystalline cellulose | 120.0 |
| Cornstarch | 20.0 |
| Magnesium stearate | 1.6 |
| Sodium lauryl sulfate | 0.2 |

The ingredients may be blended and filled into hard gelatin capsules of suitable size.

| Tablets | mg/tablet |
|---|---|
| L-Dopa | 533.3 |
| N,N-Dimethyl-5-methoxy-8-chloro-1,2,3,4-tetrahydro-1-naphthylamine | 13.3 |
| Cornstarch | 127.0 |
| Microcrystalline cellulose | 127.0 |
| Magnesium stearate | 5.4 |
| Sodium lauryl sulfate | 0.6 |

The ingredients may be blended and compressed, and the compressed pieces then broken into granules and compressed into finished tablets.

Tablets or capsules of the above formulations are appropriate for administration to patients to alleviate the symptoms of Parkinson's Disease in daily dosage ranges of about 7–80 mg/kg body weight of L-Dopa and about 2–7 mg/kg body weight of N,N-dimethyl-5-methoxy-8-chloro-1,2,3,4-tetrahydro-1-naphthylamine.

Alleviation of the symptoms of Parkinson's Disease may also be obtained by concurrent administration of L-Dopa and N,N-dimethyl-5-methoxy-8-chloro-1,2,3,4-tetrahydro-1-naphthylamine in separate tablets or capsules at the dosages stated above.

What is claimed is:

1. A pharmaceutical composition useful in the control of the symptoms of Parkinson's disease which comprises the L-isomer of 3,4-dihydroxyphenylalanine and a compound of the structure

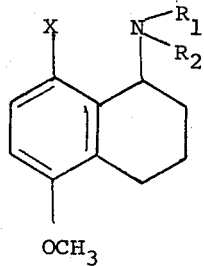

or the pharmaceutically acceptable acid addition salts thereof; wherein X is chlorine, bromine, hydrogen or methoxy; and $R_1$ and $R_2$ are each hydrogen or alkyl of from 1 to 3 carbon atoms, the ratio of said 3,4-dihydroxyphenylalanine to said compound being about 40:1 to about 1:1.

2. The composition of claim 1 wherein X is chlorine, $R_1$ and $R_2$ are each methyl, and said compound is the hydrochloric acid salt.

3. A method of controlling the symptoms of Parkinson's disease with the L-isomer of 3,4-dihydroxyphenylalanine which comprises administering daily to a patient from about 7 to 80 mg/kg body weight of said 3,4-dihydroxyphenylalanine and from about 2 to 7 mg/kg body weight of a compound of the structure
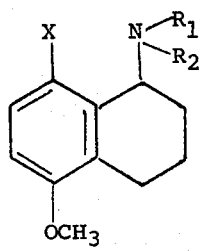
or the pharmaceutically acceptable acid addition salts thereof; wherein X is chlorine, bromine, hydrogen or methoxy; and $R_1$ and $R_2$ are each hydrogen or alkyl of from 1 to 3 carbon atoms.
* * * * *